United States Patent [19]

Kimura et al.

[11] 4,060,550
[45] Nov. 29, 1977

[54] NOVEL N'-ACYLATED PHENYL-HYDRAZINE AND -HYDRAZONE DERIVATIVES

[75] Inventors: Michio Kimura, Minoo; Shigeho Inaba, Takarazuka; Hisao Yamamoto, Nishinomiya, all of Japan

[73] Assignee: Sumitomo Chemical Company, Limited, Japan

[21] Appl. No.: 651,831

[22] Filed: Jan. 23, 1976

Related U.S. Application Data

[62] Division of Ser. No. 439,035, Feb. 4, 1974, Pat. No. 3,974,145, which is a division of Ser. No. 173,700, Aug. 20, 1971, Pat. No. 3,812,112.

[30] Foreign Application Priority Data

Aug. 26, 1970 Japan .................................. 45-75198
Dec. 9, 1970 Japan .................................. 45-109769
Dec. 9, 1970 Japan .................................. 45-109771
Feb. 15, 1971 Japan .................................. 46-6887
Feb. 16, 1971 Japan .................................. 46-7492
Aug. 27, 1970 Japan .................................. 45-75818

[51] Int. Cl.² .......................................... C07C 103/133
[52] U.S. Cl. .............................. 260/340.5 R; 548/300; 260/346.22; 260/345.3; 260/326.34; 260/332.2 A; 260/347.3; 260/557 B; 260/557 H; 260/558 H; 260/559 H; 260/562 H; 542/421; 542/439; 542/428; 424/274; 424/324; 260/250 B; 260/256.4 R; 260/295 C; 260/295 H; 260/302 R; 260/302 D; 260/307 R; 260/307 H; 260/340.3; 260/326.13 A; 260/326.14 A; 260/275; 260/561 H
[58] Field of Search .......... 260/561 H, 562 H, 559 H, 260/558 H, 240.3, 240.5, 240 J, 240 K

[56] References Cited

U.S. PATENT DOCUMENTS 3,669,960  6/1972  Okamoto et al. ................. 260/240 J
3,687,969  8/1972  Alexander et al. ............... 260/558 H Primary Examiner—Arthur P. Demers
Attorney, Agent, or Firm—Stevens, Davis, Miller & Mosher

[57] ABSTRACT

Indolylacetic acid derivatives, which have excellent anti-inflammatory, antipyretic and analgesic activities, represented by the formula,

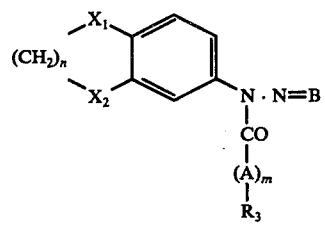

wherein $X_1$ and $X_2$ are each methylene; A is an unsubstituted ethylenically unsaturated hydrocarbon chain having up to 5 carbon atoms; $m$ is 0 or 1; $n$ is 1 or 2; $R_3$ is alkyl having up to 4 carbon atoms; cycloalkyl having 3 to 7 carbon atoms, unsubstituted or $C_1$–$C_4$ alkyl-, nitro-, trifluoromethyl-, methylenedioxy-, ethylenedioxy- or halogen-substituted phenyl, or halogen-, $C_1$–$C_4$ alkyl- or phenyl-substituted or benzene ring-condensed $C_3$–$C_7$ cycloalkyl, or unsubstituted or halogen-, $C_1$–$C_4$ alkyl- or phenyl-substituted or benzene ring-condensed $C_5$–$C_6$ cycloalkenyl; and B is

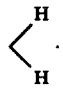

10 Claims, No Drawings

NOVEL N'-ACYLATED PHENYL-HYDRAZINE AND -HYDRAZONE DERIVATIVES

This is a division of application Ser. No. 439,035 filed Feb. 4, 1974, now U.S. Pat. No. 3,974,145, which in turn is a division of application Ser. No. 173,700, filed Aug. 20, 1971, now U.S. Pat. No. 3,812,112.

This invention relates to novel indolylacetic acid derivatives, and process for the production thereof.

More particularly, this invention pertains to novel indolylacetic acid derivatives represented by the formula

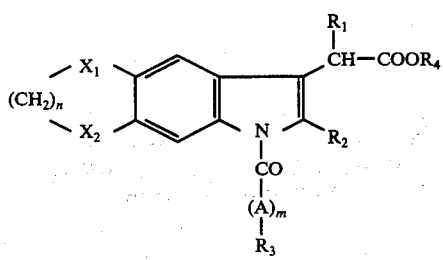

wherein each $X_1$ and $X_2$ is a member selected from the group consisting of oxygen and methylene; A is a member selected from the group consisting of unsubstituted saturated hydrocarbon chain having up to 5 carbon atoms, unsubstituted ethylenically unsaturated hydrocarbon chain having up to 5 carbon atoms, and substituted saturated or substituted ethylenically unsaturated hydrocarbon chain having up to 5 carbon atoms in which the substituents are selected from the group consisting of halogen or phenyl, the hydrocarbon chain being straight or branched one; m is 0 or 1; n is 1 or 2; each $R_1$ and $R_2$ is a member selected from the group consisting of hydrogen and alkyl having up to 4 carbon atoms; $R_3$ is a member selected from the group consisting of alkyl having up to 4 carbon atoms, unsubstituted or lower alkyl-, lower alkoxy-, lower alkylthio-, nitro-, cyano-, methylenedioxy-, ethylenedioxy- or halogen-substituted aryl, each of said alkyl, alkoxy and alkylthio substituents containing up to 4 carbon atoms, or unsubstituted, or halogen-, alkyl- or phenyl-substituted or benzene ring-condensed, saturated or unsaturated mono- or poly-alicyclic group, or alkyl group substituted by said alicyclic group, or unsubstituted or methyl-, ethyl- or halogen-substituted 5- or 6-membered heterocyclic ring group containing oxygen, sulfur or nitrogen atom; $R_4$ is a member selected from the group consisting of alkyl having up to 4 carbon atoms or hydrogen, or M radical, said M being a cation, and methods for the production and pharmaceutical use of the same.

The term "halogen" includes chlorine, bromine, iodine and fluorine. The term "alkyl" includes both straight and branched hydrocarbon chains, such as methyl, ethyl, propyl, isopropyl, butyl, isobutyl, and the like.

In the compounds represented by the aforesaid formula (I), a group of the formula

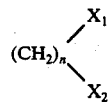

may be of methylenedioxy, ethylenedioxy, ethyleneoxy, trimethyleneoxy, trimethylene or tetramethylene. Preferred are the compounds of formula (I) wherein n is 1. Especially preferred are the compounds of formula (I) wherein

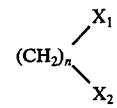

radical is methylenedioxy or trimethylene.

When $R_3$ is aryl or substituted aryl, it includes, preferably, less than three fused rings. The aryl radical may be further substituted in the aromatic rings thereof with hydrocarbon groups or with functional substituents. Suitable hydrocarbon groups are these containing up to nine carbon atoms including such radicals as phenyl, benzyl, tolyl, and the lower alkyls such as methyl, ethyl, isopropyl, tertiarybutyl and the like. The term "functional substituent", as used herein, means a substituent other than hydrogen or hydrocarbon. Preferred aryl radical is phenyl or naphthyl radical. The aromatic rings of such groups may contain, and in the preferred compounds do contain, at least one functional substituent. This substituent may be alkyl such as methyl, ethyl, isopropyl, tertiarybutyl and the like, alkoxy such as methoxy, ethoxy, isopropoxy, allyloxy and the like, alkylthio such as methylthio, ethylthio or propylthio, nitro, cyano, trifluoromethyl, methylenedioxy, ethylenedioxy, or halogen such as chlorine, bromine, fluorine or iodine. In the preferred compounds, the aryl radical is phenyl and the functional substituent is in the para position of the aromatic ring.

When $R_3$ is saturated or unsaturated mono- or polyalicyclic group, it includes cycloalkyl, cycloalkenyl, benzene ring-condensed cycloalkyl or benzene ring-condensed cycloalkenyl. The alicyclic group may further substituted in the alicyclic and/or benzene rings thereof with at least one substituent. The substituent may be halogen such as chlorine, bromine or fluorine, alkyl such as methyl, ethyl, isopropyl or tertiarybutyl, or phenyl. Examples of cycloalkyl includes cyclopropyl, cyclobutyl, cyclopentyl, cyclohexyl, 2-methylcyclopropyl, 3-methylcyclopentyl, 2-methylcyclopentyl, 1-phenyl-1-cyclopentyl and dimethylcyclopropyl. Examples of cycloalkenyl includes cyclohexenyl, cyclopentenyl, tetrahydro-m-tolyl, tetrahydro-p-tolyl, cyclopentadienyl and cyclohexadienyl. Examples of the benzene ring-condensed alicyclic group includes indanyl, tetrahydro-naphthyl, 1-methyl-indanyl, indenyl, methylindenyl and dihydronaphthyl. Examples of alicyclic-substituted alkyl group includes cyclohexeneyl-methyl, 3-methyl-cyclohexeneylmethyl, indenylmethyl, 1-(2'-indenyl)ethyl and 1-(3'-indenyl)ethyl.

When $R_3$ is hetrocyclic ring group, it includes saturated and unsaturated heterocyclic group consisting five- and six-membered heterocyclic ring containing oxygen, sulfur and nitrogen atom. Examples of the heterocyclic radicals include furyl, thienyl, pyrrolyl, thiazolyl, thiadiazolyl, pyrazinyl, pyridyl, pyrazolidinyl, pyridazinyl, pyrazolyl, imidazolyl, oxazolyl, pyrimidinyl and isoxazolyl rings. Said heterocyclic radicals may be further substituted in the rings thereof with methyl, ethyl or halogen.

Among novel 3-indolylacetic acid derivatives of the present invention, there are many useful compounds, which have excellent anti-inflammatory activity with low toxicity. Illustratively, 1-(p-chlorobenzoyl)-2-methyl-5,6-methylenedioxy-3-indolylacetic acid, 1-(p-chlorobenzoyl)-2-methyl-6,7-dihydrofuro[2,3-f]-3-indolylacetic acid, 1-(p-fluorobenzoyl)-2-methyl-5,6-methylenedioxy-3-indolylacetic acid and 1-cinnamoyl-2-methyl-5,6-methylenedioxy-3-indolylacetic acid show remarkable inhibitory actions for carrageenin-induced edema in rats, and the $ED_{50}$ of each compound is 17 mg/kg, 45 mg/kg, 14 mg/kg and 25 mg/kg respectively.

In contrast to the above facts, the many compounds of this invention are markedly low in toxicity, and even when over 500 mg/kg of these compounds are orally administrated respectively to rats and mice, they scarcely show toxic symptoms and occult bleeding is negative in feces thereof. Mevertheless, the activities of these compounds are very much higher than those of known compounds, i.e. 1,2-diphenyl-3,5-dioxo-4-n-butylpyrazolidine (phenylbutazone) and oxyphenbutazone. Therefore, these compounds are markedly valuable in practical use.

The novel indolylacetic acids of this invention and the corresponding salts are effective in the prevention and inhibition of granuloma tissue formation. They are of value in the treatment of arthritic and dermatological disorders and in like conditions which are responsive to treatment with anti-inflammatory agents. In addition, the compounds of this invention have useful degree of antipyretic and analgesic activities. For these purposes, they are administered in the form of pharmaceutical compositions, normally orally, e.g., in tablets or capsules, the suitable dosage depending, of course, upon the particular compound being used and the type of severity of the condition being treated. Although the suitable dosage of these compounds of this invention to be used in such manner depends in the compound employed and the particular type of disease condition to be treated, useful oral dosage levels of the compounds are in the range of 1.0 – 2000 mg per day depending on the activity of the specific compound to be used and on the reaction sensitivity of the patient.

Accordingly, an object of the present invention is to provide novel and useful indolylacetic acid derivatives and salts thereof which have excellent pharmacological properties.

Another object is to provide process for producing such novel and useful indolylacetic acid derivatives or salts thereof.

A further object is to provide novel $N^1$-acylated hydrazine and hydrazone derivative which are the key intermediates for the chemical synthesis of the indolylacetic acid derivatives.

A still further object is to provide pharmaceutical compositions containing such novel and useful indolylacetic acid derivatives or salts thereof.

Other objects and merits of the present invention will be apparent from the following description.

In order to accomplish these objects, the present invention provides novel 1-acyl-3-indolylacetic acid derivatives represented by the formula (I).

Further, the present invention provides a process for producing novel indolylacetic acid derivatives of the formula (I), which comprises treating an $N^1$-acylated compound represented by the formula

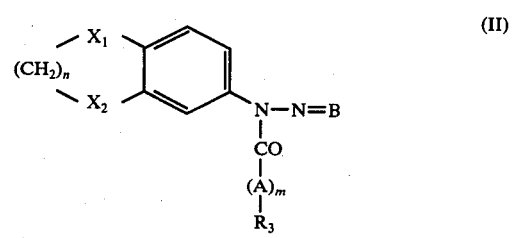

wherein $X_1$, $X_2$, A, $m$, $n$ and $R_3$ are the same as defined above, and B is a member selected from the group consisting of

of Z (wherein Z is a nitrogen protecting system comprising at least one readily removable group), with an aliphatic acid derivative represented by the formula

wherein $R_1$, $R_2$ and $R_4$ are the same as defined above.

Still further, the present invention provides a process for producing novel indolylacetic acid derivatives of the formula (I), and salts thereof, which comprises treating an $N^1$-acylated phenylhydrazine derivative [falling under the scope of formula (II)] represented by the formula

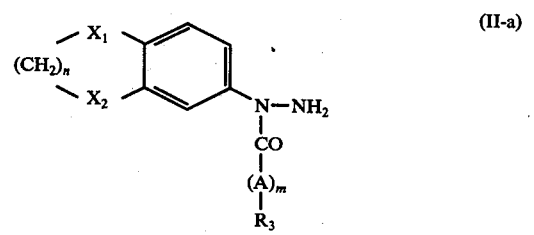

wherein $X_1$, $X_2$, A, $R_3$, $m$ and $n$ are the same as defined above, with a aliphatic acid derivative of the formula (III).

Still further, the present invention provides a process for producing novel indolylacetic acid derivatives, of the formula (I), which comprises treating a compound [falling under the scope of formula (II)] represented by the formula

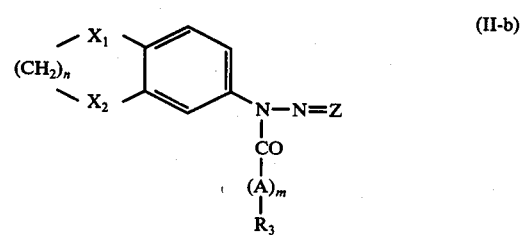

wherein $X_1$, $X_2$, A, $R_3$, $m$ and $n$ are the same as defined above, and Z is a nitrogen protecting system comprising at least one readily removal group, with a aliphatic acid derivative of the formula (III).

Still further, the present invention provides a process for producing novel indolylacetic acid derivatives of the formula (I), which comprises treating a compound represented by the formula

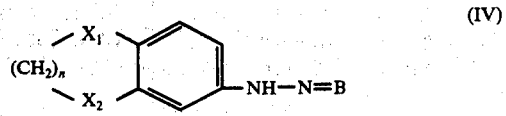

(IV)

wherein $X_1$, $X_2$, B and $n$ are the same as defined above, with an acid halide represented by the formula

(V)

wherein A, $R_3$ and $m$ are the same as defined above, and hal is halogen, to give $N^1$-acylated compound of the formula (II), and treating the resultant $N^1$-acylated compound with an aliphatic acid derivative of the formula (III).

In the formula (II) and (II-b) the protecting system Z may be comprised of a group or groups which are readily removable by conventional procedures, well documented in the literature. Systems for which the character Z is assigned and which will function efficaciously for the purposes of the present invention are those which consist of, for example, a ketone or aldehyde residual group, one hydrogen group and one hydrocarbon carboxylic acyl group, or one hydrogen group and one sulfo radical. The ketone or aldehyde residual group employed is not particularly critical and any of these may be used. Suitable examples of these are derived from acetaldehyde, chloral, benzaldehyde, acetal, ethyl acetacetate, methoxy acetone, diphenyl ketone or the like. Other ketone or aldehyde residue well known in the art can also be employed. The hydrocarbon carboxylic acyl group used in the present invention will contain less than twelve carbon atoms and may be of a straight, branched, cyclic or cyclic-aliphatic chain structure. They may be of saturated, unsaturated or aromatic and optionally substituted by functional groups, such as hydroxy, nitro, amino, halogen and the like. Example of the hydrocarbon carboxylic acyl group includes formyl, acetyl, propionyl, trifluoroacetyl, benzoyl, and the like. Example of the sulfo radical includes sulfonic acid rest, alkali metal or alkali earth metal sulfonate or ammonium sulfonate rest.

The starting materials of formula (IV) may be synthesized by methods well known to those skilled in the art. Thus, the starting compounds of the formula (IV) wherein B is

may be prepared by the manner described in the article written by Macbeth et al in J. Chem. Soc. 1951 2968. The compounds of the formula (IV) wherein R is a nitrogen protecting system may be prepared from the corresponding phenylhydrazine derivative of the formula (IV) wherein B is

by protecting the terminal amino function thereof with a suitable protecting system by well established techniques. For example, the compounds of the formula (IV) wherein B is

is reacted with a ketone or aldehyde to yield the corresponding compounds of the formula (IV) where B is a ketone residual group or an aldehyde residual group.

The compounds of formula (V) are converted into the corresponding $N^1$-acylated compounds of formula (II) by treating the former compounds with an acid halide of formula (V).

The acid halide (V) may be chloride, bromide or iodide; and the chloride is preferred from a commercial point of view. The reaction is carried out in a solvent in the presence of hydrogen halide acceptor. As the hydrogen halide acceptor, a tertiary amine, for example, pyridine, picoline, triethylamine or dimethylaniline can be used. These hydrogen halide acceptors themselves can be used as solvents. Inert solvents such as ether, benzene, toluene, xylene and tetrahydrofuran can also be used as reaction solvents in the presence of equimolar or larger amount of these hydrogen halide acceptors. The reaction proceeds at room temperature in many cases, and even below 0° C. in some kind of solvent used. The exothermic reaction is generally complete in a few minutes to several hours. After the reaction is completed, the produced hydrogen halide salt of the hydrogen halide acceptor is filtered off and the filtrate is concentrated under a reduced pressure, or the reaction mixture is poured into water when a water-soluble solvent like pyridine is used as the solvent, and the aimed $N^1$-acylated phenylhydrazone compound is easily obtained as crystals or an oily substance. These products can be purified with an appropriate solvent.

When the compound of the formula (IV) wherein B is

is acylated with an acid halide of the formula (V), the reaction is often accompanied by formation of by-product such as $N^2$-acylated compound or $N^1$, $N^2$-diacylated compound. The objective $N^1$-acylated derivative (II-a) is separated and purified by removing the by-products by a suitable method such as column chromatography. However, the purification of the $N^1$-acylated compound is not necessary, because only the $N^1$-acylated derivative is concerned with the following reaction in the present invention.

When a compound having a comparatively weak

bonding is used as a derivative (IV) or under severe conditions of reaction, an $N^1$-acylated phenylhydrazine derivative (II-a) is directly obtained in place of an $N^1$-acylated phenylhydrazone derivative (II-b).

The compounds of the formula (II-a) is also prepared from the compounds of the formula (II-b) by removing the protecting system. The removal of the protecting system is conducted by utilizing conventional procedures well established in the art.

The thus-obtained $N^1$-acylated compound are treated with an aliphatic acid derivative of the formula (III) to yield the objective indolylacetic acid derivatives of the formula (I).

This reaction is carried out by heating in the presence or absence, of an adequate condensing agent and with or without an organic solvent. The yield is very high.

The present reaction proceeds smoothly without a solvent but it is preferable to use a suitable solvent in many cases. As the solvent, organic acids, for example, acetic acid, formic acid, propionic acid, lactic acid, butyric acid, non-polar organic solvents, for example, cyclohexane, n-hexane, benzene, toluene, and other organic solvents, such as dioxane and N,N-dimethyl formamide are used in the ring formation reaction. When an alcohol is used as a solvent in this reaction, a corresponding ester of indole aliphatic acid is produced.

Generally, the reaction proceeds at a temperature within a range of 50° to 200° C., but a temperature within a range of 65° C to 95° C. is preferable. The reaction proceeds rapidly and is generally completed in a short time, mostly in one or two hours. The condensing agent is not needed in some cases but desirable results are generally achieved by using a condensing agent. The condensing agent includes inorganic acids such as hydrochloric acid, sulfuric acid and phosphoric acid, metal halides such as zinc chloride and copper chloride, heavy metal powder such as copper powder, Grignard's reagents, boron fluorides, polyphosphoric acid or ion-exchange resins. Hydrochloric acid or the like is required in an equimolar or larger amount, while copper powder or the like may be in a small amount.

In after-treatment, the reaction mixture is allowed to stand at room temperature or in a refrigerator (about 5° C.), and then a large amount of crystals of the product is obtained.

When crystals are not produced, the reaction mixture is concentrated under reduced pressure, or water, acetic acid-water or petroleum ether in adequately added to the mixture. And then, beautiful crystals can be obtained. Ether, acetone, acetone-water, alcohol, alcohol-water, benzene and acetic acid are generally preferred as a solvent for recrystallizing the present compound. The produced crystals are collected by filtration and, generally, they are washed with an aqueous solution of acetic acid, alcohol-water, water or petroleum ether before they are dried. Objective products are generally crystalline, but oily products are sometimes given in ester compounds.

Reaction solvents, reaction conditions, condensing agents and recrystallization solvents which have been mentioned above are only presented as illustrative of the present invention and are not limitative, in any way.

The 1-acyl-3-indolylacetic acid derivative of the formula (I) wherein $R_4$ is hydrogen can be converted into the corresponding salts by treating the free acid with a base under mild conditions. In this manner there may be obtained alkaline metal salts such as a sodium, potassium, aluminium or magnesium salts or alkaline earth metal salts, such as barium or calcium salts. Salts of organic amines such as dimethylamine, morpholine, choline, diethylaminoethanol, methylcyclohexylamine, hystidine, arginine, lysine, thiamine, pyridoxamine or glucosamine may be obtained by reacting the acid with the appropriate organic base. Salts of heavy metals such as zinc and iron salts are also within the purview of this invention.

This invention is further disclosed in the following Examples of more preferred embodiments thereof, which are presented for the purpose of illustration and it is not intended to limit the scope of the invention.

EXAMPLE 1

To a solution of 13g of 3,4-methylenedioxyphenylhydrazine in 100 ml of ether was added dropwise 4.1 g of 80 % acetaldehyde at 0° – 5° C over a period of 20 minutes.

After stirring for an additional two hours at 0° – 5° C, the ethereal solution was separated, and dried over anhydrous sodium sulfate. The ether was evaporated, and the resultant residue was distilled to give 11.5 g of acetaldehyde-3,4-methylenedioxyphenylhydrazone having a boiling point of 113° – 115° C (0.07 mmHg).

Infrared absorption: $\Theta$ max 3300, 2850, 1620, 920 cm$^{-1}$

EXAMPLE 2

To a solution of 2 g of acetaldehyde-3,4-methylenedioxyphenylhydrazone in 2 g of pyridine and 50 ml of ether was added dropwise 1.96 g of p-chlorobenzoylchloride at 0° – 5° C.

The reaction mixture was stirred at 0° – 5° C for 2 hours, and at a room temperature for 5 hours. The reaction mixture was poured into water and the crude product was obtained.

The resultant crude product was recrystallized from ethanol to give 3 g of acetaldehyde-$N^1$-(p-chlorobenzoyl)-3,4-methylenedioxyphenylhydrazone having a melting point of 143° – 145° C.

Infrared absorption: $\Theta$ max 1640, 1620, 1580 cm$^{-1}$

In a manner similar to that described in Example 2, the following compounds were prepared:

acetaldehyde-$N^1$-(p-fluorobenzoyl)-3,4-methylenedioxyhydrazone, infrared absorption: $\Theta$ max 1660, 1620, 1600 cm$^{-1}$ acetaldehyde-$N^1$-cinnamoyl-3,4-methylenedioxyphenylhydrazone, melting point: 140° – 142° C acetaldehyde-$N^1$-(3',4'-methylenedioxybenzoyl)-3,4-methylenedioxyphenylhydrazone, infrared absorption: $\Theta$ max 1640, 1610, 1600 cm$^{-1}$ acetaldehyde-$N^1$-(5'-indanecarbonyl)-3,4-methylenedioxyphenylhydrazone, melting point: 151° – 153° C acetaldehyde-$N^1$-nicotinoyl-3,4-methylenedioxyphenylhydrazone, melting point: 138° – 139.5° C acetaldehyde-$N^1$-caproyl-3,4-methylenedioxyphenylhydrazone, melting point: 48° – 49° C acetaldehyde-$N^1$-sorboyl-3,4-methylenedioxyphenylhydrazone, melting point: 187° – 189° C acetaldehyde-$N^1$-(2'-furanacryloyl)-3,4-methylenedioxyphenylhydrazone acetaldehyde-$N^1$-(1'-indanecarbonyl)-3,4-methylenedioxyphenylhydrazone acetaldehyde-$N^1$-naphthenoyl-3,4-methylenedioxyphenylhydrazone acetaldehyde-$N^1$-cyclopropanecarbonyl-3,4-methylenedioxyphenylhydrazone

EXAMPLE 3

Hydrogen chloride gas was bubbled into a solution of 1.8 g of acetaldehyde-$N^1$-(p-chlorobenzoyl)-3,4- methylenedioxyphenylhydrazone in 40 ml of ethanol at 0° – 3° C for 3 hours. The ethanol was removed at 20° – 25° C under reduced pressure.

To the residue were added 300 ml of ether to give 1.99 g of $N^1$-(p-chlorobenzoyl)-3,4-methylenedioxyphenylhydrazine hydrochloride having a melting point of 189° – 190° C (decomp.).

Infrared absorption: $\Theta$ max 1670, 1580 cm$^{-1}$

In a manner similar to that described in Example 3, the following compounds were prepared:

$N^1$-(p-fluorobenzoyl)-3,4-methylenedioxyphenylhydrazine hydrochloride, infrared absorption: $\Theta$ max 1600, 1670 cm$^{-1}$ $N^1$-(p-methylbenzoyl)-3,4-methylenedioxyphenylhydrazine hydrochloride, infrared absorption: $\Theta$ max 1660, 1600 cm$^{-1}$ $N^1$-cinnamoyl-3,4-methylenedioxyphenylhydrazine hydrochloride, melting point 190° – 191° C $N^1$-(3',4'-methylenedioxybenzoyl)-3,4-methylenedioxyphenylhydrazine hydrochloride, infrared absorption: $\Theta$ max 1680, 1690 cm$^{-1}$ $N^1$-(5'-indanecarbonyl)-3,4-methylenedioxyphenylhydrazine hydrochloride, melting point: 203° – 204° C $N^1$-nicotinoyl-3,4-methylenedioxyphenylhydrazine hydrochloride, melting point: 213° – 214° C $N^1$-caproyl-3,4-methylenedioxyphenylhydrazine hydrochloride, melting point: 153° – 155° C $N^1$-sorboyl-3,4-methylenedioxyphenylhydrazine hydrochloride, melting point: 175° – 178° C $N^1$-(2'-furanacryloyl)-3,4-methylenedioxyphenylhydrazine hydrochloride $N^1$-(1'-indanecarbonyl)-3,4-methylenedioxyphenylhydrazine hydrochloride $N^1$-naphthenoyl-3,4-methylenedioxyphenylhydrazine hydrochloride $N^1$-cyclopropanecarbonyl-3,4-methylenedioxyphenylhydrazine hydrochloride

EXAMPLE 4

A mixture of 1.9 g of $N^1$-(p-chlorobenzoyl)-3,4-methylenedioxyphenylhydrazine hydrochloride and 20 g of levulinic acid was heated for 1 hour at 55° – 60° C and for 3 hours at 80° – 90° C. The reaction mixture was cooled to a room temperature, and poured into 200 ml of water. The precipitates were collected by filtration and washed with water. The crystals obtained by twice recrystallizing from acetone-water (5 : 1) gave 1.19 g of 1-(p-chlorobenzoyl)-2-methyl-5,6-methylenedioxy-3-indolylacetic acid having a melting point of 217° – 218° C.

Infrared absorption: $\Theta$ max 1700, 1680, 1580 cm$^{-1}$

In a manner similar to that described in Example 4, the following compounds were prepared:

1-cinnamoyl-2-methyl-5,6-methylenedioxy-3-indolylacetic acid, melting point: 190° – 191° C 1-(p-fluorobenzoyl)-2-methyl-5,6-methylenedioxy-3-indolylacetic acid, melting point: 238° – 240° C 1-(p-methylbenzoyl)-2-methyl-5,6-methylenedioxy-3-indolylacetic acid, melting point: 204° – 206° C 1-(3',4'-methylenedioxybenzoyl)-2-methyl-5,6-methylenedioxy-3-indolylacetic acid, melting point: 198° – 200° C 1-(5'-indanecarbonyl)-2-methyl-5,6-methylenedioxy-3-indolylacetic acid, melting point: 190° – 192° C 1-caproyl-2-methyl-5,6-methylenedioxy-3-indolylacetic acid, melting point: 125° – 127° C 1-sorboyl-2-methyl-5,6-methylenedioxy-3-indolylacetic acid, melting point: 177° – 178° C 1-nicotinoyl-2-methyl-5,6-methylenedioxy-3-indolylacetic acid, melting point: 229° – 229.5° C 1-(1'-indanecarbonyl)-2-methyl-5,6-methylenedioxy-3-indolylacetic acid 1-naphthenoyl-2-methyl-5,6-methylenedioxy-3-indolylacetic acid 1-cyclopropanecarbonyl-2-methyl-5,6-methylenedioxy-3-indolylacetic acid 1-(2'-furanacryloyl)-2-methyl-5,6-methylenedioxy-3-indolylacetic acid

EXAMPLE 5

To a solution of 1.2 g of 1-(p-chlorobenzoyl)-2-methyl-5,6-methylenedioxy-3-indolylacetic acid in 50 ml of acetone was added dropwise a solution of 0.132 g of sodium hydroxide in 10 ml of water at 0° – 2° C. The reaction mixture was stirred for an additional 2 hours at 15° – 20° C and filtered.

The precipitates so obtained were washed three times with 10 ml of acetone to give 1.2 g of sodium 1-(p-chlorobenzoyl)-2-methyl-5,6-methylenedioxy-3-indolylacetate.

Infrared absorption: $\Theta$ max 1680, 1560 cm$^{-1}$

EXAMPLE 6

To a solution of 17 g of 3,4-ethylenedioxyphenylhydrazine in 100 ml of ether was added dropwise 11 g of 80 % acetaldehyde at 5° – 10° C over a period of 30 minutes. After stirring for an additional two hours at 5° – 10° C, the ethereal solution was separated, and dried over anhydrous sodium sulfate. The ether was evaporated, and the resultant residue was distilled to give 15.4 g of acetaldehyde-3,4-ethylenedioxyphenylhydrazone having a boiling point of 139° – 142° C (0.15 mmHg).

Infrared absorption: $\Theta$ max 3400, 2800 – 3000, 1620, 1590 cm$^{-1}$

EXAMPLE 7

To a solution of 6.4 g of acetaldehyde-3,4-ethylenedioxyphenylhydrazone in 3.9 g of pyridine and 50 ml of ether were added dropwise 5.2 g of p-methylbenzoylchloride at 0° – 5° C. The reaction mixture so obtained was stirred at 0° – 5° C for 2 hours, and at a room temperature for 5 hours. The resultant reaction mixture was poured into water to give a crude product.

The resultant crude product was recrystallized from ethanol to give 5.8 g of acetaldehyde-$N^1$-(p-methylbenzoyl)-3,4-ethylenedioxyphenylhydrazone having a melting point of 121° – 122.9° C.

Infrared absorption: $\Theta$ max 1650, 1620 cm$^{-1}$

In a manner similar to that described in Example 7, the following compounds were prepared:

acetaldehyde-$N^1$-(p-chlorobenzoyl)-3,4-ethylenedioxyphenylhydrazone, melting point: 184' – 187° C acetaldehyde-$N^1$-cinnamoyl-3,4-ethylenedioxyphenylhydrazone, melting point: 135° – 137° C acetaldehyde-$N^1$-(p-fluorobenzoyl)-3,4-ethylenedioxyphenylhydrazone acetaldehyde-$N^1$-(3',4'-methylenedioxybenzoyl)-3,4-ethylenedioxyphenylhydrazone, melting point: 148.5° – 150° C acetaldehyde-$N^1$-(5'-indanecarbonyl)-3,4-ethylenedioxyphenylhydrazone, melting point: 141° – 142.5° C acetaldehyde-$N^1$-(1'-indanecarbonyl)-3,4-ethylenedioxyphenylhydrazone acetaldehyde-$N^1$-cyclopropanecarbonyl-3,4-ethylenedioxyphenylhydrazone

EXAMPLE 8

Hydrogen chloride gas was bubbled into a solution of 5.5 g acetaldehyde-N$^1$-(p-methylbenzoyl)-3,4-ethylenedioxyphenylhydrazone ethylenedioxyphenylhydrazone in 30 ml of ethanol at 0° – 5° C for 3 hours. The ethanol was removed at a room temperature under reduced pressure. To the residue was added 200 ml of ether to obtain 5 g of N$^1$-(p-methylbenzoyl)-3,4-ethylenedioxyphenylhydrazine hydrochloride, having a melting point of 166° – 168° C.

Infrared absorption: ν max 1660, 1600 cm$^{-1}$

In a manner similar to that described in Example 8, the following compounds were prepared:

N$^1$-(p-chlorobenzoyl)-3,4-ethylenedioxyphenylhydrazine hydrochloride, infrared absorption: ν max 1670, 1590 cm$^{-1}$ N$^1$-cinnamoyl-3,4-ethylenedioxyphenylhydrazine hydrochloride, infrared absorption: ν max 1680, 1620 cm$^{-1}$ N$^1$-(p-fluorobenzoyl)-3,4-ethylenedioxyphenylhydrazine hydrochloride N$^1$-(3',4'-methylenedioxybenzoyl)-3,4-ethylenedioxyphenylhydrazine hydrochloride, melting point: 167° – 168° C N$^1$-(5'-indanecarbonyl)-3,4-ethylenedioxyphenyl hydrazine hydrochloride, melting point: 181° – 182° C N$^1$-(1'-indanecarbonyl)-3,4-ethylenedioxyphenylhydrazine hydrochloride N$^1$-(cyclopropanecarbonyl-3,4-ethylenedioxyphenylhydrazine hydrochloride

EXAMPLE 9

A mixture of 5 g of N$^1$-(p-methylbenzoyl)3,4-ethylenedioxyphenylhydrazine hydrochloride and 30 g of levulinic acid was heated for 3 hours at 85° – 90° C. The reaction mixture was cooled to a room temperature, and poured into 200 ml of water. crude product was recrystallized twice from ethyl acetate to give 1-(p-methylbenzoyl)-2-methyl-5,6-ethylenedioxy-3-indolylacetic acid having a melting point of 170° – 171° C.

Infrared absorption: ν max 1710, 1670, 1610, 1590 cm$^{-1}$

In a manner similar to that described in Example 9, the following compounds were prepared:

1-(p-chlorobenzoyl)-2-methyl-5,6-ethylenedioxy-3-indolylacetic acid, melting point: 162° – 163° C 1-cinnamoyl-2-methyl-5,6-ethylenedioxy-3-indolylacetic acid, melting point: 203° – 204.5° C 1-(p-fluorobenzoyl)-2-methyl-5,6-ethylenedioxy-3-indolylacetic acid 1-(3',4'-methylenedioxybenzoyl)-2-methyl-5,6-ethylenedioxy-3-indolylacetic acid, infrared absorption: ν max 1730, 1640, 1610 cm$^{-1}$ 1-(5'-indanecarbonyl)-2-methyl-5,6-ethylenedioxy-3-indolylacetic acid, melting point: 202.5° – 203.5° C 1-(1'-indanecarbonyl)-2-methyl-5,6-ethylenedioxy-3-indolylacetic acid 1-cyclopropanecarbonyl-2-methyl-5,6-ethylenedioxy-3-indolylacetic acid

EXAMPLE 10

To a solution of 19.5 g of 2,3-dihydrobenzofuran-5-hydrazine in 100 ml of ether was added 6.2 g of 80 % acetaldehyde at 0° – 5° C over a period of 30 minutes. After stirring for an additional two hours at 0° – 5° C, the ethereal solution was separated and dried over anhydrous sodium sulfate. The ether was evaporated, and the resultant residue was distilled to give 10.5 g of acetaldehyde-2,3-dihydrobenzofurane-5-hydrazone having a boiling point of 126° – 128° C (0.05 mmHg).

Infrared absorption: Θ max 3300, 1600, 1640, 1660 cm$^{-1}$

EXAMPLE 11

To a solution of 2 g of acetaldehyde-2,3-dihydrobenzofuran-5-hydrazone in 2 g of pyridine and 50 ml of ether was added a solution of 1.9 g of p-chlorobenzoyl-chloride in 10 ml of ether at 0° – 5° C. The reaction mixture was stirred at 0° – 5° C for 3 hours, and at a room temperature for 5 hours. The reaction mixture was poured into water and the other layer was separated and washed with 30 ml of water three times. After drying over anhydrous sodium sulfate, ether was evaporated to give acetaldehyde-N$^1$-(p-chlorobenzoyl)2,3-dihydrobenzofurane-5-hydrazone as an oil.

Infrared absorption: Θ max 1650, 1620, 1590 cm$^{-1}$

In a manner similar to that described in Example 11, the following compounds were prepared:

acetaldehyde-N$^1$-cinnamoyl-2,3-dihydrobenzofurane-5-hydrazone acetaldehyde-N$^1$-naphthenoyl-2,3-dihydrobenzofurane-5-hydrazone acetaldehyde-N$^1$-(p-methylbenzoyl)-2,3-dihydrobenzofurane-5-hydrazone acetaldehyde-N$^1$-cyclopropanecarbonyl-2,3-dihydrobenzofurane-5-hydrazone

EXAMPLE 12

Hydrogen chloride gas was bubbled into a solution of 1.8 g of acetaldehyde N$^1$-(p-chlorobenzoyl)-2,3-dihydrabenzofurane-5-hydrazone in 40 ml of ethanol at 0° – 5° C for 1 hour. After stirring at 0°– 5° C for an additional three hours, ethanol was removed at 20° – 25° C under reduced pressure. The resultant residue was triturated with 300 ml of ether to give 1.7 g of N$^1$-(p-chlorobenzoyl)-2,3-dihydrobenzofurane-5-hydrazine hydrochloride.

Infrared absorption: Θ max 1660, 1590 cm$^{-1}$

In a manner similar to that described in Example 12, the following compounds were prepared:

N$^1$-cinnamoyl-2,3-dihydrobenzofurane-5-hydrazine hydrochloride

N$^1$-naphthenoyl-2,3-dihydrobenzofurane-5-hydrazine hydrochloride

N$^1$-(p-methylbenzoyl)-2,3-dihydrobenzofurane-5-hydrazine hydrochloride

N$^1$-cyclopropanecarbonyl-2,3-dihydrobenzofurane-5-hydrazine hydrochloride

EXAMPLE 13

A mixture of 1.7 g of N$^1$-(p-chlorobenzoly)-2,3-dihydrobenzofurane-5-hydrazine hydrochloride and 30 g of levulinic acid was heated at 85° – 90° C for 3 hours. The reaction mixture was cooled to a room temperature and poured into 200 ml of water to give a crude 1-(p-chlorobenzoyl)-2-methyl-6,7-dihydrofuro[2,3-f]-3-indorylacetic acid.

The crystals obtained by twice recrystallizing from 95 % ethanol showed a melting point of 216° – 218° C and infrared absorption of Θ max: 1680, 1700, 1930 cm$^{-1}$ In a manner similar to that described in Example 13, the following compounds were prepared:

1-cinnamoyl-2-methyl-6,7-dihydrofuro[2,3-f]-3-indolylacetic acid 1-naphthenoyl-2-methyl-6,7-dihydrofuro[2,3-f]-3-indolylacetic acid 1-(p-methylbenzoyl)-2-methyl-6,7-dihydrofuro-[2,3-f]-3-indolylacetic acid 1-cyclopropanecarbonyl-2-methyl-6,7-dihydrofuro-[2,3-f]-3-indolylacetic acid

EXAMPLE 14

To a solution of 26 g of 3,4-cyclopentenophenylhydrazine in 250 ml of ether, was added 8.2 g of 80 % acetaldehyde at 0° – 5° C for over a period of 30 minutes. After stirring for an additional two hours at 0° – 5° C, the ethereal solution was separated, and dried over anhydrous sodium sulfate. The ether was evaporated, and the resultant residue was distilled to give 20 g of acetaldehyde-3,4-cyclopentenophenylhydrazone having a boiling point of 113° – 115° C (0.06 mmHg).

Infrared absorption: Θ max 3300, 2900, 1600, 1580 cm$^{-1}$

EXAMPLE 15

To a solution of 10 g of acetaldehyde-3,4-cyclopentenophenylhydrazone in 6.8 g of pyridine and 80 ml of ether were added 9.56 g of cinnamoylchloride at 0° – 5° C.

The reaction mixture was stirred at 0° – 5° C for 2 hours and at a room temperature for 5 hours. The reaction mixture was poured into water and the crude product was obtained. Recrystallization from ethanol gives 10 g of acetaldehyde-N$^1$-cinnamoyl-3,4-cyclopentenophenylhydrazone having a melting point of 138° – 140° C.

Infrared absorption: Θ max 1660, 1610 cm$^{-1}$

In a manner similar to that described in Example 15, the following compounds were prepared:

acetaldehyde-N$^1$-(p-chlorobenzoyl)-3,4-cyclopentenophenylhydrazone, melting point: 119° – 122° C acetaldehyde-N$^1$-(p-fluorobenzoyl)-3,4-cyclopentenophenylhydrazone, melting point: 113° – 114° C acetaldehyde-N$^1$-(p-methylbenzoyl)-3,4-cyclopentenophenylhydrazone, melting point: 105° – 106° C acetaldehyde-N$^1$-(3',4'-methylenedioxybenzoyl)-3,4-cyclopentenophenylhydrazine, melting point: 111° – 113° C acetaldehyde-N$^1$-(5'-indanecarbonyl)-3,4-cyclopentenophenylhydrazone, melting point: 110° – 112° C acetaldehyde-N$^1$-(1'-indanecarbonyl)-3,4-cyclopentenophenylhydrazone, melting point: 115° – 117° C acetaldehyde-N$^1$-cyclopropanecarbonyl-3,4-cyclopentenophenylhydrazone, melting point: 111° – 113° C acetaldehyde-N$^1$-(α-chlorophenylacetyl)-3,4-cyclopentenophenylhydrazone, melting point: 116° – 118° C acetaldehyde-N$^1$-(2'-furanacryloyl)-3,4-cyclopentenophenylhydrazone, melting point: 176.5° – 178° C

EXAMPLE 16

Hydrogen chloride gas was bubbled into a solution of 10 g of acetaldehyde-N$^1$-cinnamoyl-3,4-cyclopentenophenylhydrazone in 60 ml of ethanol at 0° – 5° C for 3 hours. After stirring at 0° – 5° C for an additional 5 hours, ethanol was removed at a room temperature under reduced pressure. The residue was triturated with 300 ml of ether to obtain 10.1 g of N$^1$-cinnamoyl-3,4-cyclopentenophenylhydrazine hydrochloride having a melting point of 150° C (decomp.)

Infrared absorption: Θ max 1700 – 1660, 1620, 1570 cm$^{-1}$

In a manner similar to that described in Example 16, the following compounds were prepared:

N$^1$-(p-chlorobenzoyl)-3,4-cyclopentenophenylhydrazine hydrochloride, melting point: 194° – 196° C N$^1$-(p-fluorobenzoyl)-3,4-cyclopentenophenylhydrazine hydrochloride, melting point: 180° – 181° C N$^1$(p-methylbenzoyl)-3,4-cyclopentenophenylhydrazine hydrochloride, melting point: 176° – 177° C N$^1$(3',4'-methylenedioxybenzoyl)-3,4-cyclopentenophenylhydrazine hydrochloride, melting point: 184° – 186° C N$^1$-(5'-indanecarbonyl)-3,4-cyclopentenophenylhydrazine hydrochloride, melting point: 179° – 181° C N$^1$(1'-indanecarbonyl)-3,4-cyclopentenophenylhydrazine hydrochloride, melting point: 211° – 212° C N$^1$-cyclopropanecarbonyl-3,4-cyclopentenophenylhydrazine hydrochloride, melting point: 158.5° – 159° C N$^1$-(α-chlorophenylacetyl)-3,4-cyclopentenophenylhydrazine hydrochloride, melting point: 137° – 139° C N$^1$-(2'-furanacryloyl)-3,4-cyclopentenophenylhydrazine hydrochloride, melting point: 178° – 179° C

EXAMPLE 17

A mixture of 8 g of N$^1$-cinnamoyl-3,4-cyclopentenophenylhydrazine hydrochloride and 50 g of levulinic acid was heated at 90° C for 1 hour and at 95° – 100° C for 2 hours. The reaction mixture was cooled to a room temperature, and poured into 300 l of water to give a crude 1-cinnamoyl-2-methyl-5,6-cyclopenteno-3-indolylacetic acid. The crystals obtained by twice recrystallizing from n-hexane-acetone (3 : 1) showed a melting point of 144° – 146° C.

Infrared absorption: Θ max 1710, 1670, 1630, 1600 cm$^{-1}$

In a manner similar to that described in Example 17, the following compounds were prepared:

1-(p-chlorobenzoyl)-2-methyl-5,6-cyclopenteno-3-indolylacetic acid, melting point: 199° – 203° C 1-(p-fluorobenzoyl)-2-methyl-5,6-cyclopenteno-3-indolylacetic acid, melting point: 208.5° – 209.5° C 1-(p-methylbenzoyl)-2-methyl-5,6-cyclopenteno-3-indolylacetic acid, melting point: 205° – 206° C 1-(3',4'-methylenedioxybenzoyl)-2-methyl-5,6-cyclopenteno-3-indolylacetic acid, melting point: 198° – 201° C 1-(5'-indanecarbonyl)-2-methyl-5,6-cyclopenteno-3-indolylacetic acid, melting point: 210° – 211.5° C 1-(1'-indanecarbonyl)-2-methyl-5,6-cyclopenteno-3-indolylacetic acid, melting point: 180.7° – 182.7° C 1-cyclopropanecarbonyl-2-methyl-5,6-cyclopenteno-3-indolylacetic acid, melting point: 178° – 181° C 1-(α-chlorophenylacetyl)-2-methyl-5,6-cyclopenteno-3-indolylacetic acid, melting point: 178° – 180° C 1-(2'-furanacryloyl)-2-methyl-5,6-cyclopenteno-3-indolylacetic acid, infrared absorption: Θ max 1710, 1670, 1600 cm$^{-1}$

EXAMPLE 18

To a solution of 24 g of 3,4-cyclohexanophenylhydrazine in 200 ml of ether was added dropwise 22 g of 80 % acetaldehyde at 0° – 5° C for over a period of 40 minutes. After stirring for an additional two hours at 5° – 10° C, the ethereal solution was separated and dried over anhydrous sodium sulfate. The ether was evaporated, and the residue was distilled to give 30 g of acetaldehyde-3,4-cyclohexanophenylhydrazone having a boiling point of 131° – 133.5° C (0.09 mmHg).

Infrared absorption: Θ max 3300, 2900, 1610 cm$^{-1}$

EXAMPLE 19

To a solution of 9 g of acetaldehyde-3,4-cyclohexanophenylhydrazone in 6 g of pyridine and 50 ml of ether was added 8.7 g of p-chlorobenzoyl chloride at 0° – 5° C. The reaction mixture was stirred at 0° – 5° C for 3 hours and at a room temperature for 5 hours. The reaction mixture was poured into water and the crude product was obtained. Recrystallization from ethanol gave 10.9 g of acetaldehyde-N$^1$-(p-chlorobenzoyl)-3,4-cyclohexanophenylhydrazone having a melting point of 128° – 130° C.

Infrared absorption: Θ max 1650, 1620, 1580 cm$^{-1}$

EXAMPLE 20

Hydrogen chloride gas was bubbled into a solution of 10 g of acetaldehyde N$^1$-(p-chlorobenzoyl)-3,4-cyclohexanophenylhydrazone in 50 ml of ethanol at 0° – 3° C for 3 hours. The ethanol was removed at 20° – 25° C under reduced pressure. To the residue was triturated with 300 ml of ether to give 5.3 g of N$^1$-(p-chlorobenzoyl)-3,4-cyclohexanophenylhydrazine hydrochloride having a melting point of 180° – 181° C (decomp.).

Infrared absorption: Θ max 1660, 1570 cm$^{-1}$

EXAMPLE 21

A mixture of 10.3 g of N$^1$-(p-chlorobenzoyl)-3,4-cyclohexanophenylhydrazine hydrochloride and 45 g of levulinic acid was heated at 85° – 92° C for 3 hours. The reaction mixture was cooled to a room temperature, and poured into 500 ml of water. The crude crystals were filtered, and washed three times with 20 ml of water. Recrystallization from ether-petroleum ether (3 : 1) gave 9.5 g of 1-(p-chlorobenzoyl)-2-methyl-5,6-cyclohexano-3-indolylacetic acid having a melting point of 179° – 181° C.

Infrared absorption: Θ max 1640 – 1680, 1580 cm$^{-1}$

EXAMPLE 22

A mixture of 3.06 g of N$^1$-(p-methylbenzoyl)-3,4-methylenedioxyphenylhydrazine hydrochloride and 1.69 g of α-methyl levulinic acid in 30 ml of acetic acid was heated for 3 hours at 80° – 90° C. The reaction mixture was cooled to a room temperature, and poured into 200 ml of water. The water layer was removed by decantation. This operation was repeated three times to give the crude product. Recrystallization from methanol-water (5 : 1) and from methanol again gave 2 g of α-{1-(p-methylbenzyloxy)-2-methyl-5,6-methylenedioxy-3-indolyl}propionic acid having a melting point of 172° – 175° C Infrared absorption: Θ max 1700, 1600 cm$^{-1}$ In a manner similar to that described in Example 22, the following compounds were prepared:

α-{1-(p-chlorobenzoyl)-2-methyl-5,6-methylenedioxy-3-indolyl}propionic acid

α-{1-cinnamoyl-2-methyl-5,6-methylenedioxy-3-indolyl}propionic acid

α-{1-sorboyl-2-methyl-5,6-methylenedioxy-3-indolyl}propionic acid

α-{1-(p-chlorobenzoyl)-2-methyl-5,6-ethylenedioxy-3-indolyl}propionic acid

α-{1-(p-methylbenzoyl)-2-methyl-5,6-ethylenedioxy-3-indolyl}propionic acid

α-{1-naphthenyol-2-methyl-6,7-dihydrofuro[2,3-f]-3-indolyl}propionic acid

α-{1-(p-chlorobenzoyl)-2-methyl-5,6-cyclopenteno-3-indolyl}propionic acid

α-{1-cinnamoyl-2-methyl-5,6-cyclopenteno-3-indolyl}propionic acid

α-{1-(5'-indanecarbonyl)-2-methyl-5,6-cyclopenteno-3-indolyl}propionic acid

α-{1-(1'-indanecarbonyl)-2-methyl-5,6-cyclopenteno-3-indolyl}propionic acid

α-{1-cyclopropanecarbonyl-2-methyl-5,6-cyclopenteno-3-indolyl}propionic acid

α-{1-(2'-furanacryloyl)-2-methyl-5,6-cyclopenteno-3-indolyl}propionic acid

EXAMPLE 23

A mixture of 3 g of N$^1$-cinnamoyl-N$^2$-formyl-3,4-methylenedioxyphenylhydrazine in 30 ml of levulinic acid was heated in the presence of small amount of hydrogen chloride gas at 70° – 75° C for 3 hours.

The reaction mixture was cooled to a room temperature, and added 300 ml of water to give precipitates. The precipitates was filtered and washed three times with water.

Recrystallization from acetone-water (6 : 1) gave 1-cinnamoyl-2-methyl-5,6-methylenedioxy-3-indolylacetic acid having a melting point of 190° – 191° C.

Infrared absorption: γ max 1730, 1660, 1620 cm$^{-1}$

EXAMPLE 24

A mixture of 2.5 g of N$^1$-(p-chlorobenzoyl)-N$^2$-formyl-3,4-cyclopentenophenylhydrazine in 25 g of levulinic acid was heated in the presence of small amount of sulfuric acid at 65° – 70° C for 3 hours. The reaction mixture was cooled to a room temperature and poured into 300 ml of water to give a crude product. The resultant crude product was filtered and washed three times with water.

Recrystallization from acetone-water (5 : 1) gave 1-(p-chlorobenzoyl)-2-methyl-5,6-cyclopenteno-3-indolylacetic acid having a melting point of 198° – 201° C.

Infrared absorption: Θ max 1700, 1680, 1580 cm$^{-1}$

EXAMPLE 25

A solution of 3.5 g of N$^1$-cinnamoyl-N$^2$-acetyl-3,4-cyclopentenophenylhydrazine and 10 g of levulinic acid in 50 ml of acetic acid was heated in the presence of small amount of sulfuric acid at 60° – 65° C for 3 hours. The reaction mixture was cooled to a room temperature and poured into 300 ml of water to give precipitates. The precipitates so obtained was filtered and washed three times with water.

Recrystallization from n-hexane-acetone (3 : 1) gave 1-cinnamoyl-2-methyl-5,6-cyclopenteno-3-indolylacetic acid having a melting point of 144° – 146° C.

Infrared absorption: Θ max 1710, 1670, 1630, 1600 cm$^{-1}$

EXAMPLE 26

A mixture of 3.5 g of N$^1$-(p-methylbenzoyl)-N$^2$-acetyl-3,4-cyclopentenophenylhydrazine in 20 g of levulinic acid was added a small amount of hydrogen-chloride gas.

The mixture so obtained was heated at 60° – 65° C for 3 hours.

Similarly, using the procedure described in Example 25, there was obtained 1-(p-methylbenzoyl)-2-methyl-5,6-cyclopenteno-3-indolylacetic acid. The crystals obtained by recrystallizing from acetone-water (5 : 1) showed a melting point of 205° – 206° C.

Infrared absorption: Θ max 1720, 1690, 1670, 1600 cm$^{-1}$

EXAMPLE 27

A solution of 3.5 g of N$^1$-(2'-furanacryloyl)-3,4-cyclopentenophenylhydrazine hydrochloride and 10 g ethyl levulinate in 50 ml of ethanol was heated at 80° – 85° C for 3 hours.

The reaction mixture was cooled to a room temperature, poured into 300 ml of water, and extracted three times with 50 ml of ether. The ether extract was washed with water, dried over anhydrous sodium sulfate and concentrated in vacuo. The crude product was chromatographed on 150 g of silica gel by charging with ethyl acetate and eluting with ethyl acetate to give ethyl 1-(2'-furanacryloyl)-2-methyl-5,6-cyclopenteno-3-indolylacetate.

Infrared absorption: Θ max 1710, 1630 cm$^{-1}$

EXAMPLE 28

A mixture of 8 g of sodium N$^1$-cinnamoyl-3,4-methylenedioxyphenylhydrazine-N$^2$-sulfite,

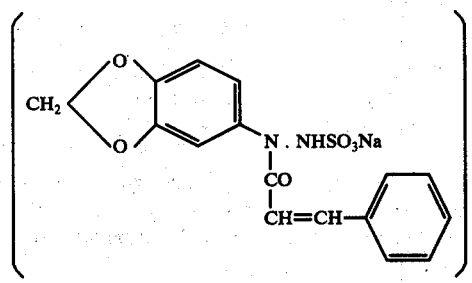

and 45 ml of levulinic acid was heated in the presence of small amount of surfuric acid at 80° – 85° C for 3 hours. The reaction mixture was cooled to a room temperature and poured into water to give 1-cinnamoyl-2-methyl-5,6-methylenedioxyl-3-indolylacetic acid. The crystals obtained by twice recrystallizing from acetone-water (5 : 1) showed a melting point of 190° – 192° C.

Infrared absorption: Θ max 1730, 1660, 1620 cm$^{-1}$

What is claimed is:

1. A compound of the formula,

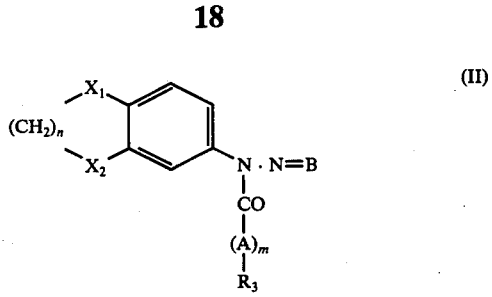

wherein $X_1$ and $X_2$ are each methylene; A is an unsubstituted ethylenically unsaturated hydrocarbon chain having up to 5 carbon atoms, m is 0 or 1; n is 1 or 2; $R_3$ is alkyl having up to 4 carbon atoms, cycloalkyl having 3 to 7 carbon atoms, unsubstituted or $C_1$–$C_4$ alkyl-, nitro-, trifluoromethyl-, methylenedioxy-, ethylenedioxy- or halogen-substituted phenyl, or halogen-, $C_1$–$C_4$ alkyl- or phenyl-substituted or benzene ring-condensed $C_3$–$C_7$ cycloalkyl, or unsubstituted or halogen-, $C_1$–$C_4$ alkyl- or phenyl-substituted or benzene ring-condensed $C_5$–$C_6$ cycloalkenyl; and B is

2. A compound according to claim 1 which is N$^1$-Cinnamoyl-3,4-cyclopentenophenylhydrazine.

3. A compound according to claim 1 which is N$^1$-(p-Chlorobenzoyl)-3,4-cyclopentenophenylhydrazine.

4. A compound according to claim 1 which is N$^1$-(p-Fluorobenzoyl)-3,4-cyclopentenophenylhydrazine.

5. A compound according to claim 1 which is N$^1$-(p-Methylbenzoyl)-3,4-cyclopentenophenylhydrazine.

6. A compound according to claim 1 which is N$^1$-(3',4'-Methylenedioxybenzoyl)-3,4-cyclopentenophenylhydrazine.

7. A compound according to claim 1 which is N$^1$-(5'-Indanecarbonyl)-3,4-cyclopentenophenylhydrazine.

8. A compound according to claim 1 which is N$^1$-(1'-Indanecarbonyl)-3,4-cyclopentenophenylhydrazine.

9. A compound according to claim 1 which is N$^1$-Cyclopropanecarbonyl-3,4-cyclopentenophenylhydrazine.

10. A compound according to claim 1 which is N$^1$-(p-Chlorobenzoyl)-3,4-cyclohexanophenylhydrazine.

* * * * *

UNITED STATES PATENT OFFICE
CERTIFICATE OF CORRECTION

Patent No. 4,060,550          Dated November 29, 1977

Inventor(s) Michio KIMURA et al

It is certified that error appears in the above-identified patent and that said Letters Patent are hereby corrected as shown below:

The additional two priority applications are relied upon by the patentees:

[30] Foreign Application Priority Data:

--    Oct. 3, 1970     Japan ................ 86964/70
--    Dec. 9, 1970     Japan ................ 109768/70    --

Signed and Sealed this

Nineteenth Day of September 1978

[SEAL]

Attest:

RUTH C. MASON  
Attesting Officer

DONALD W. BANNER  
Commissioner of Patents and Trademarks